United States Patent [19]

Ichijima et al.

[11] 4,264,723
[45] Apr. 28, 1981

[54] SILVER HALIDE COLOR PHOTOGRAPHIC MATERIALS

[75] Inventors: Seiji Ichijima; Nobuo Seto; Toshiyuki Watanabe; Nobuo Furutachi, all of Minami-ashigara, Japan

[73] Assignee: Fuji Photo Film Co., Ltd., Minami-ashigara, Japan

[21] Appl. No.: 91,663

[22] Filed: Nov. 5, 1979

[30] Foreign Application Priority Data

Nov. 6, 1978 [JP] Japan .................................. 53/136497

[51] Int. Cl.³ .............................................. G03C 1/40
[52] U.S. Cl. ..................................... 430/555; 430/387
[58] Field of Search ................................. 430/555, 387

[56] References Cited

U.S. PATENT DOCUMENTS

| 3,227,554 | 1/1966 | Barr et al. | 430/555 |
| 3,615,506 | 10/1971 | Abbott et al. | 430/555 |
| 3,930,861 | 1/1976 | van Poucke et al. | 430/387 |
| 3,930,866 | 1/1976 | Oishi et al. | 430/555 |

Primary Examiner—J. Travis Brown
Attorney, Agent, or Firm—Sughrue, Rothwell, Mion, Zinn and Macpeak

[57] ABSTRACT

Silver halide color photographic sensitive materials which comprise photographic layers containing at least one of the couplers represented by the following general formula (I):

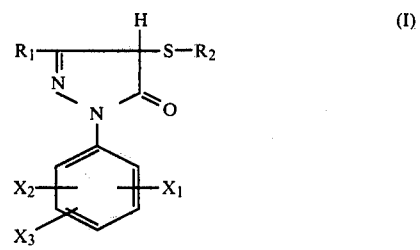

wherein $R_1$ represents an anilino group, an acylamino group or a ureido group, $R_2$ represents an alkyl group, an aralkyl group or an alkenyl group, $X_1$, $X_2$ and $X_3$ each represents a hydrogen atom, an alkyl group, a halogen atom, an alkoxy group, an aryloxy group, an acylamino group, a carbamoyl group, a sulfamoyl group, a sulfonyl group, a cyano group or an alkoxycarbonyl group and $X_1$, $X_2$ and $X_3$ may be the same or different, are disclosed.

14 Claims, No Drawings

SILVER HALIDE COLOR PHOTOGRAPHIC MATERIALS

BACKGROUND OF THE INVENTION

1. Field of the Invention

The present invention relates to color photographic materials and particularly to color photographic materials wherein the dye formation efficiency in the color development step is high, photographic properties are not influenced by variation in the pH of the color developing bath and the color images are fast to heat or light.

2. Description of the Prior Art

As magenta image forming couplers (referred to as "magenta couplers", hereinafter), various pyrazolone derivatives have been known. However, these pyrazolone derivatives have low color formation efficiency (ratio of conversion of the coupler into a dye) contained in photographic sensitive materials and so-called 4-equivalent couplers in which coupling active positions are not substituted form only about ½ mol dye per mol of the coupler.

To improve color formation efficiency, so-called 2-equivalent magenta couplers have been used in which a substituent is introduced into the coupling active position of the pyrazolone type magenta coupler by which the substituent splits off in the color development step. Examples are disclosed in U.S. Pat. Nos. 3,311,476, 3,419,391, 3,617,291 and 3,926,631. Further, magenta couplers in which a substituent is linked to the coupling position through a sulfur ion are described in U.S. Pat. No. 3,214,437 (a thiocyano group), U.S. Pat. No. 4,032,346 (an acylthio or as thioacylthio) and U.S. Pat. Nos. 3,227,554 and 3,701,783 (heterocyclic thio or arylthio).

The magenta couplers used for color photosensitive materials of the present invention have an alkylthio group at the coupling active position of the pyrazolone nucleus, and are quite different in chemical structure from couplers described in the above described U.S. Pat. Nos. 3,214,437 and 4,032,346. Further, couplers having an alkylthio group of 6 to 22 carbon atoms have been claimed in U.S. Pat. Nos. 3,227,554 and 3,701,783, but there is no description of magenta couplers having an alkylthio group in these patent specifications. The couplers having an arylthio group or a heterocyclic thio group described in U.S. Pat. Nos. 3,227,554 and 3,701,783 have been known as release inhibition type couplers (DIR couplers) in the art, which function to retard the development by interaction of the arylthio group or the heterocyclic thio group released from the coupling active position of the couplers with silver halide in the development step. Couplers of the present invention from which an alkylthio group is released are functionally different from the above-described couplers, because they do not have a release inhibiting function.

SUMMARY OF THE INVENTION

Accordingly, a first object of the present invention is to provide color photographic sensitive materials having improved color formation efficiency, reduced coupler content and reduced silver halide content.

A second object of the present invention is to provide color photographic sensitive materials in which photographic properties are less influenced by variation of pH of the color developing bath.

A third object of the present invention is to provide color photographic sensitive materials containing low cost 2-equivalent magenta couplers by a simple process.

A fourth object of the present invention is to provide color photographic materials in which silver halide is not influenced after color development processing.

A fifth object of the present invention is to provide color photographic sensitive materials which form color images which are fast to light and heat.

The above-described objects of the present invention can be effectively attained by incorporating magenta couplers in which a hydrogen atom on the coupling active position of the pyrazolone is substituted by an alkylthio group in a photosensitive silver halide emulsion layer of a silver halide color photographic light-sensitive material.

Namely, by using the above-described magenta couplers which release an alkylthio group in silver halide color photographic sensitive materials, the following effects can be obtained.

(1) Color formation efficiency of the magenta couplers is remarkably improved. Accordingly, the amount of magenta couplers used can be reduced as compared with the prior art and the amount of silver halide can be remarkably reduced, and, consequently, it is possible to reduce the thickness of the magenta image providing emulsion layer. As the result, the sharpness of images can be remarkably improved.

(2) Color photographic sensitive materials can be produced at a moderate price by the reduction of the amount of couplers used and the reduction in the amount of silver halide used.

(3) The process of color development is stabilized (photosensitive materials which are hardly influenced by variation of pH of photographic processing solutions can be obtained).

(4) Color images obtained by coupling with an oxidation product of a color developing agent (for example, a p-phenylenediamine type developing agent) are remarkably fast to light and heat (color photographs having stabilized quality can be obtained).

(5) Color photographic sensitive materials having stabilized quality can be obtained, in which abnormal coloring by development does not occur when allowed to stand in the presence of formaldehyde before development.

(6) Color photographic sensitive materials in which the granularity of color images after development is excellent can be obtained.

The magenta couplers which release the alkylthio group used in the present invention are represented by the formula (I):

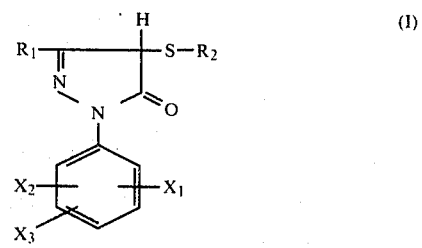

wherein $R_1$ represents an anilino group, an acylamino group or a ureido group, $R_2$ represents an aralkyl group, an alkyl group having 1 to 22 carbon atoms or an alkenyl group, $X_1$, $X_2$ and $X_3$ each represents a hydrogen atom, an alkyl group, a halogen atom, an alkoxy group, an aryloxy group, an acylamino group, a carbamoyl group, a sulfamoyl group, a sulfonyl group, a cyano group or an alkoxycarbonyl group, and $X_1$, $X_2$ and $X_3$ may be the same or different.

DETAILED DESCRIPTION OF THE INVENTION

The anilino group of $R_1$ may be substituted with one or more of a halogen atom, an alkyl group, an aralkyl group, an alkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an alkylcarbonyloxy group, an arylcarbonyloxy group, a sulfamoyl group, a carbamoyl group, an alkylcarbonylamino group, an arylcarbonylamino group, a dialkylcarbonylamino group, a diarylcarbonylamino group, a ureido group, a thioureido group, a sulfonamino group, an alkoxycarbonylamino group, an aryloxycarbonylamino group, a heterocyclic ring group, an alkylsulfonyloxy group, an arylsulfonyloxy group, an alkylsulfonyl group, an arylsulfonyl group, an alkylthio group, an arylthio group, an alkylsulfinyl group, an arylsulfinyl group, an alkylamino group, a dialkylamino group, an anilino group, an N-arylamino group, an N-alkylanilino group, an N-alkylcarbonylanilino group, an N-arylcarbonylanilino group, an imido group, a 1-hydantoinyl group, a 2,4-dioxo-3-oxazolidinyl group and a hydroxy group, wherein the sulfamoyl group, the carbamoyl group, the ureido group, the thioureido group and the sulfamino group may be substituted with one or more of an alkyl group or an aryl group; the heterocyclic ring group may be a 5- or 6-membered ring including one or more hetero atoms such as oxygen, sulfur and nitrogen, which may be condensed with a benzene nucleus; where the aforesaid alkyl moieties have 1 to 32 carbon atoms and the aforesaid moieties have 6 to 32 carbon atoms.

The acylamino group of $R_1$ represents an alkaneamido group, wherein an alkane moiety has 1 to 32 carbon atoms, or a benzamido group, which can be substituted with one or more of the same group of substituents as the aforesaid anilino group.

The ureido group of $R_1$ represents an alkylureido group, wherein an alkyl moiety has 1 to 32 carbon atoms, or a phenylureido group, which can be substituted with one or more of the same groups of substituents as the aforesaid anilino group.

An anilino and an acylamino group are preferred as $R_1$ group.

In greater detail, $R_1$ represents an anilino group (for example, a phenylamino group, an o-chlorophenylamino group, a 2,4-dichlorophenylamino group, a 2,4-dichloro-5-methoxyphenylamino group, a 2-chloro-5-tetradecanamidophenylamino group, a 2-chloro-5-[α-(2,4-di-t-aminophenoxy)-butyramido]-phenylamino group, a 2-chloro-5-[(3-octadecenyl)-succinimido]phenylamino group or a 2-chloro-5-{α-[(3-t-butyl-4-hydroxy)phenoxy]tetradecanamido}-phenylamino group, etc.). Alternatively, $R_1$ represents an acylamino group (for example, an acetylamino group, a butyramido group, an α-(3-pentadecylphenoxy)butyramido group, an n-tetradecanamido group, an α-(2,4-di-t-amylphenoxy)butyramido group, a 3-[α-(2,4-di-t-amylphenoxy)butyramido]benzamido group, a benzamido group or a 3-acetylamidobenzamido group, etc.), or a ureido group (for example, a phenylureido group, a methylureido group or a 3-[α-(2,4-di-t-amylphenoxy)-butyramido]phenylureido group, etc.

$X_1$, $X_2$ and $X_3$ each represents a hydrogen atom, a straight chain, branched chain or cyclic alkyl group having 1 to 32 carbon atoms (for example, a methyl group or an ethyl group, etc.), a halogen atom (for example, a chlorine atom, a bromine atom or a fluorine atom), a straight chain, branched chain or cyclic alkoxy group having 1 to 32 carbon atoms (for example, a methoxy group or an ethoxy group, etc.), a mono- or bicyclic aryloxy group having 6 to 32 carbon atoms (for example, a phenyloxy group or a naphthyloxy group, etc.), an acylamino group, which may be an aliphatic acylamino group having 1 to 33 carbon atoms or an aromatic acylamino group having 7 to 33 carbon atoms (for example, an acetylamino group or an α-(2,4-di-t-amylphenoxy)butyramido group, etc.), a carbamoyl group, which may be an alkylcarbamoyl group, wherein the alkyl moiety contains 1 to 32 carbon atoms or an arylcarbamoyl group, wherein the aryl moiety contains 6 to 32 carbon atoms (for example, a methylcarbamoyl group or a phenylcarbamoyl group, etc.), a sulfamoyl group including alkylsulfamoyl groups, wherein the alkyl moiety contains 1 to 32 carbon atoms or arylsulfamoyl groups, wherein the aryl moiety contains 6 to 32 carbon atoms (for example, a methylsulfamoyl group or a phenylsulfamoyl group, etc.), a sulfonyl group, which may be an alkylsulfonyl group, wherein the alkyl moiety contains 1 to 32 carbon atoms or an arylsulfonyl group, wherein the aryl moiety contains 6 to 32 carbon atoms (for example, an ethylsulfonyl group, a butylsulfonyl group, a methylsulfonyl group, or a phenylsulfonyl group, etc.), a cyano group or an alkoxycarbonyl group (for example, a methoxycarbonyl group or a tetradecyloxycarbonyl group, etc.). $X_1$, $X_2$ and $X_3$ each preferably represents a halogen atom, an alkyl group, an alkoxy group, an acylamino group, a cyano group, an alkoxycarbonyl group, etc.

$R_2$ represents a straight chain or branched chain alkyl group having 1 to 22 carbon atoms, which may be substituted. Examples of the straight chain alkyl group include a methyl group, an ethyl group, a propyl group, a butyl group, an octyl group, a dodecyl group, a tetradecyl group, an octadecyl group and a heptadecyl group. Examples of the branched chain alkyl group include an i-propyl group and a tert-butyl group. Further, $R_2$ may represent a monocyclic aralkyl group having 7 to 32 carbon atoms (for example, a benzyl group or a 2-phenylethyl group) or a straight chain or branched chain alkenyl group having 2 to 32 carbon atoms (for example, a propenyl group).

The alkyl, aralkyl and alkenyl groups represented by $R_2$ may be substituted by substituents selected from a halogen atom, a nitro group, a cyano group, an aryl group, an alkoxy group, an aryloxy group, a carboxyl group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, and a hydroxy group.

Among couplers represented by the general formula (I), those in which $R_2$ is an alkyl group having preferably 1 to 15, particularly preferably 1 to 5 carbon atoms are particularly preferred because the dyes formed have good fastness.

Examples of magenta couplers in accordance with the present invention are listed below. These examples are representative and are not to be construed as limiting.

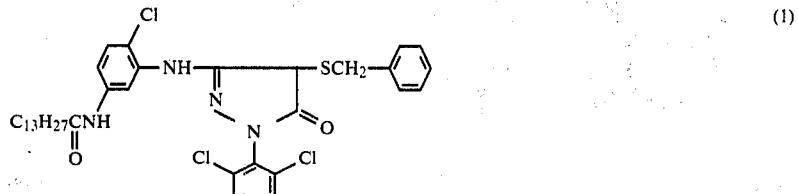

(1)

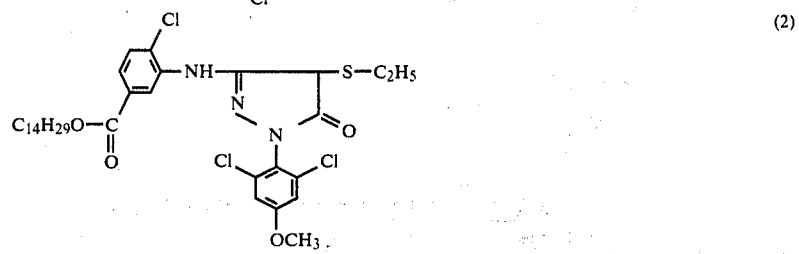

(2)

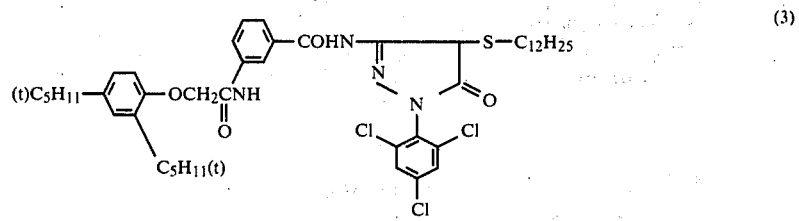

(3)

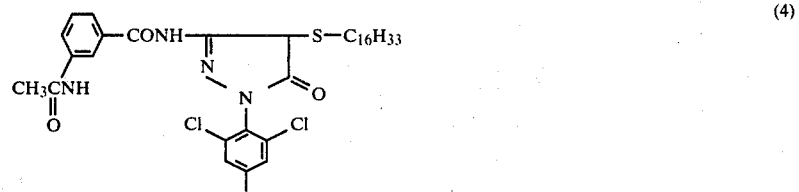

(4)

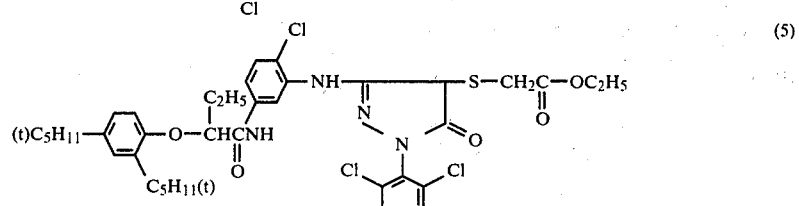

(5)

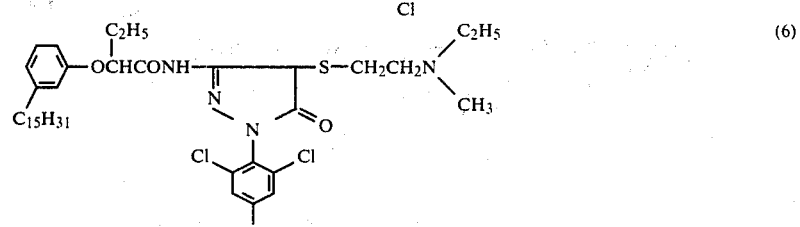

(6)

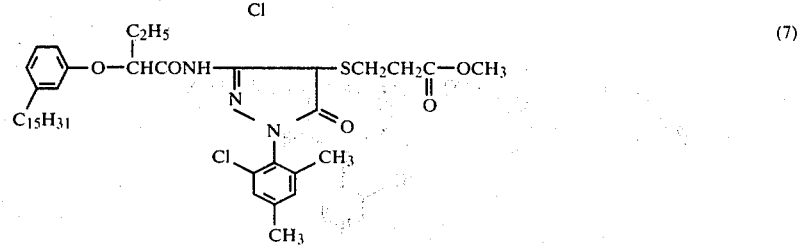

(7)

-continued
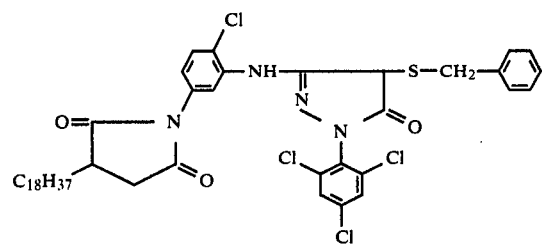 (8)
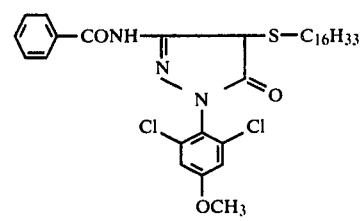 (9)
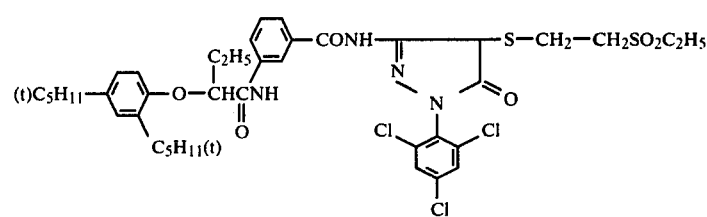 (10)
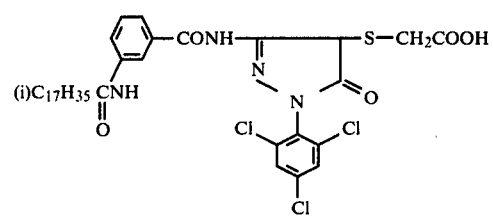 (11)
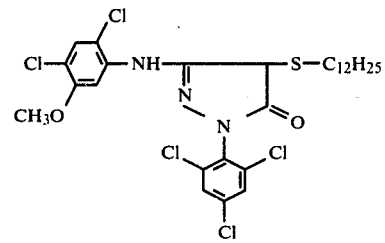 (12)
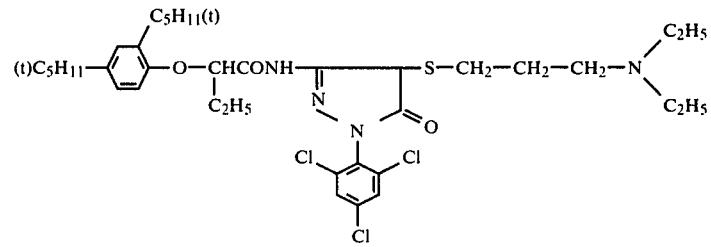 (13)
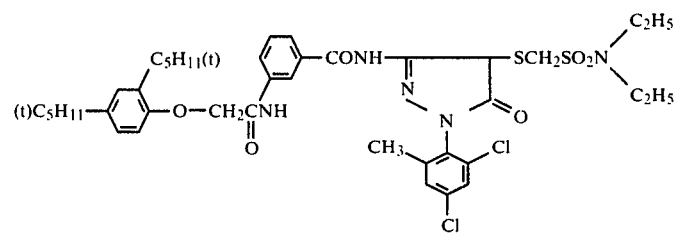 (14)

-continued
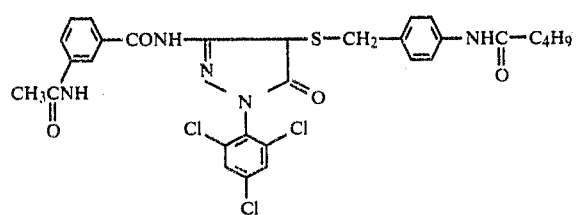 (15)
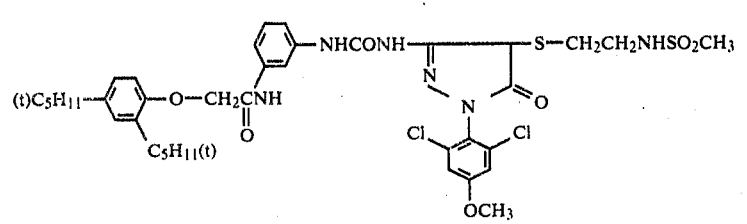 (16)
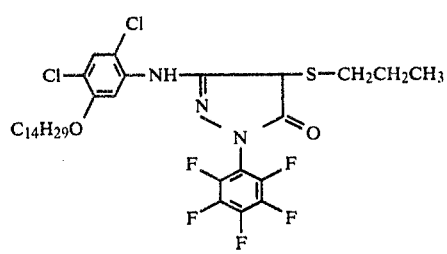 (17)
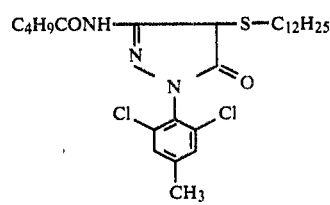 (18)
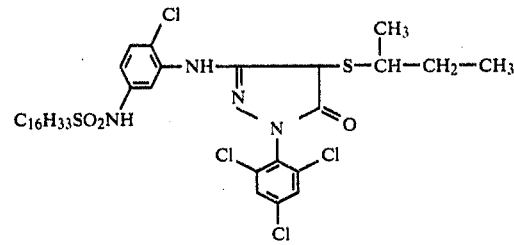 (19)
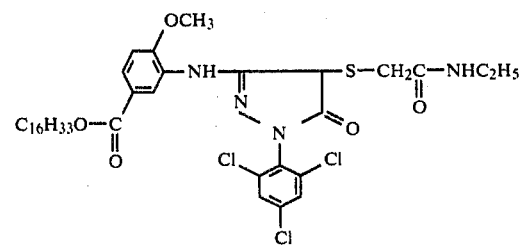 (20)
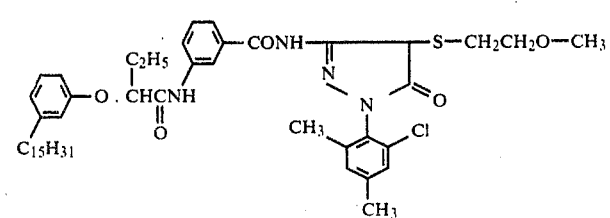 (21)

-continued
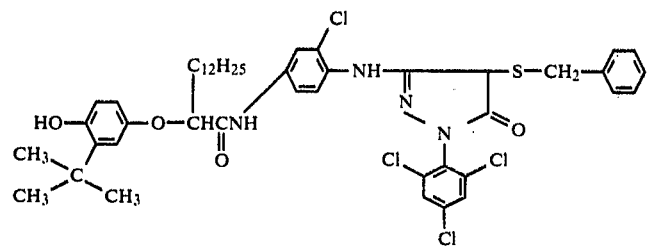 (22)
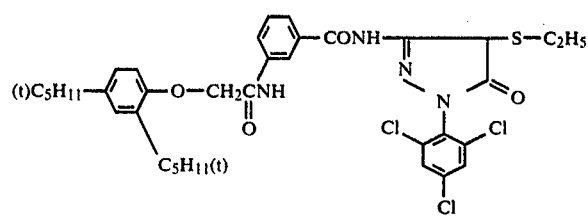 (23)
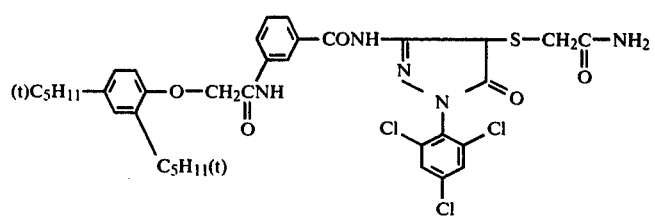 (24)
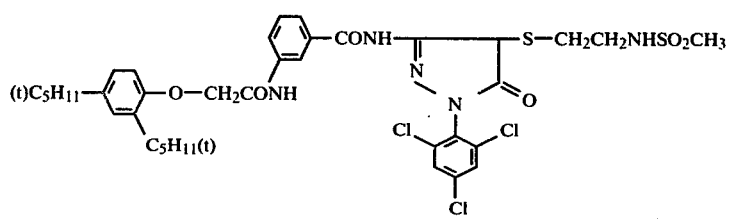 (25)
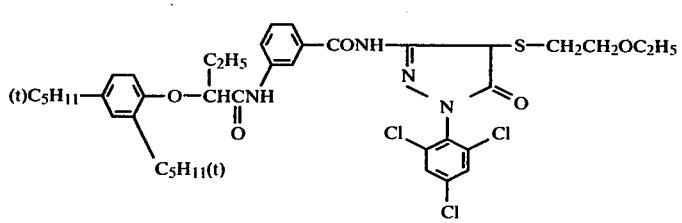 (26)
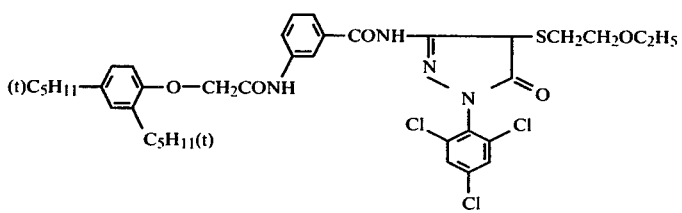 (27)
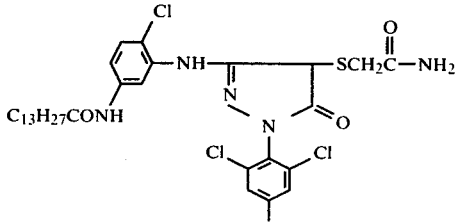 (28)

-continued
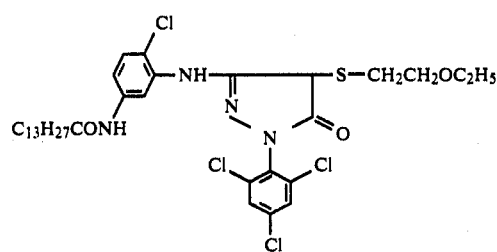 (29)
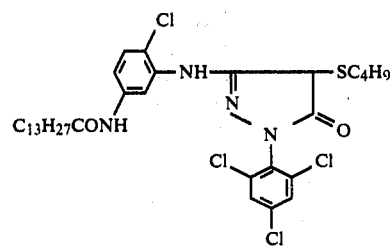 (30)
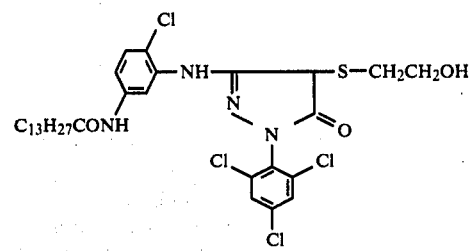 (31)
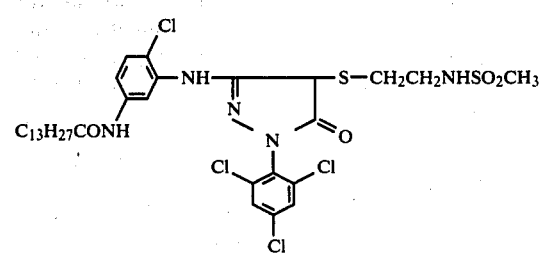 (32)
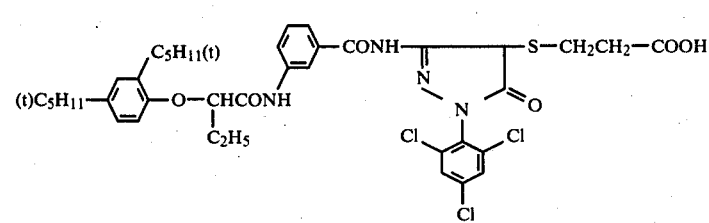 (33)
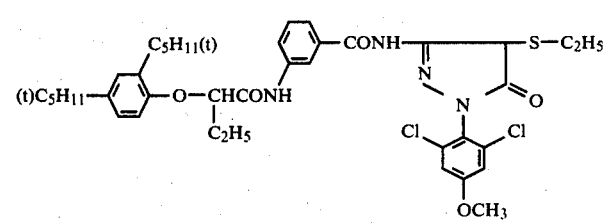 (34)
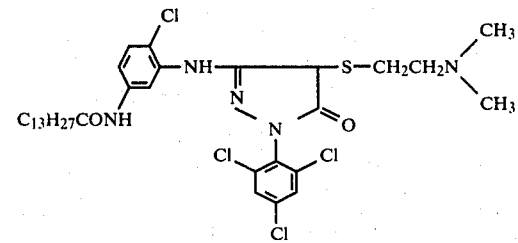 (35)

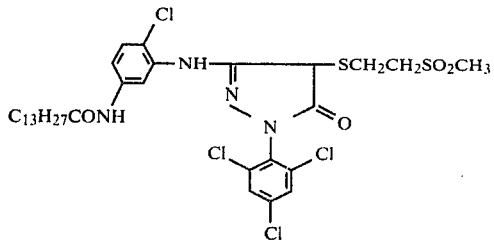

-continued
(36)

The couplers of the present invention can be prepared by reference to Synthesis Methods 1 and 2 below.

SYNTHESIS METHOD 1

1 to 1.5 mols of an S-alkyl-thioisothioureahydrochloride per mol of a 4-position-unsubstituted-5-pyrazolone coupler are added to a solvent such as an alcohol, a carboxylic acid and nonaprotic polar solvents. Further, 1 to 1.5 mols of a base (for example, a potassium carbonate, a triethylamine, etc.) per mol of the above-described coupler are added to the mixture and the mixture is stirred at a temperature of 0° to 100° C. to obtain 4-alkylthio-5-pyrazolone in a high yield.

SYNTHESIS METHOD 2

A 4-position-unsubstituted-5-pyrazolone coupler is dissolved in a solvent such as an alcohol or a nonaprotic polar solvent (for example, dimethylformamide, etc.) 1 to 2 mols of thiourea per mol of the above-described coupler is added thereto and further 1 to 1.5 mols of a bromine per mol of coupler is added dropwise slowly in this order, then the mixture is stirred at a temperature of 0° to 50° C. to isolate a 4-(5-oxo-pyrazolonyl)isothiourea. The urea derivative is dissolved in a solvent such as an alcohol (for example, a methanol, an ethanol, etc.), a carboxylic acid (for example, an acetic acid) and a nonaprotic polar solvent (for example, a dimethylformamide, etc.), 2 to 5 mols of a base per mol of an isothiourea is added thereto and the mixture is stirred at a temperature of 0° to 50° C. and then 1 to 1.5 mols of an alkyl halide per mol of an isothiourea is added to the mixture and the mixture is stirred at a temperature of 0° to 50° C. to obtain a 4-alkylthio-5-pyrazolone in a high yield.

Examples of the synthesis of typical couplers of the present invention are described below.

SYNTHESIS EXAMPLE 1

Production of 1-(2-chloro-4,6-dimethyl)phenyl-3-pentadecanamido-4-dodecylthio-5-oxo-2-pyrazoline (Compound (18))

3.2 g of 1-(2-chloro-4,6-dimethyl)-3-pentadecanamido-5-pyrazolone was dissolved in 80 ml of 80% ethanol (ratio by volume of ethanol:water=4:1) and 0.8 g of potassium carbonate was added thereto. A solution prepared by dissolving 3.2 g of S-n-dodecylthioisothiourea hydrochloride in 30 ml of ethanol was added dropwise thereto over 5 minutes with stirring while heating on a steam bath, and the mixture was stirred for 10 minutes. After cooling rapidly under a water stream, 100 ml of ethyl acetate was added thereto and the mixture was washed twice with water. After drying the ethyl acetate layer with anhydrous sodium sulfate, sodium sulfate was removed and the solvent was removed by condensing under a reduced pressure. The residue was crystallized with n-hexane. The resulting crystals were recrystallized with n-hexane to obtain 4.2 g of Coupler (18) having a melting point of 47° to 48° C.

Elemental Analysis for $C_{28}H_{44}ClN_3O_2S$: Theoretical value (%): H: 8.49; C: 64.40; N: 8.05. Experimental value (%): H: 8.54; C: 64.24; N: 8.10.

SYNTHESIS EXAMPLE 2

Production of 1-(2,4,6-trichlorophenyl)-3-(2,4-dichloro-5-methoxyanilino)-4-dodecylthio-5-oxo-2-pyrazoline (Compound (12))

15.1 g of 1-(2,4,6-trichlorophenyl)-3-(2,4-dichloro-5-methoxyanilino)-5-pyrazolone was dissolved in 500 ml of 80% ethanol (ratio by volume of ethanol:water=4:1), and 2.5 g of potassium carbonate was added thereto. A solution prepared by dissolving 10.4 g of S-(n-dodecylthio)isothiourea hydrochloride in 100 ml of ethanol was added dropwise thereto over 10 minutes with stirring while heating on a steam bath, and the mixture was stirred for another 10 minutes. After cooled rapidly under a water stream, 300 ml of ethyl acetate was added thereto, and the mixture was washed twice with water. After drying the ethyl acetate layer with anhydrous sodium sulfate, sodium sulfate was removed and the solvent was removed by condensing under a reduced pressure. The residue was crystallized with acetonitrile. The resulting crystals were recrystallized with acetonitrile-ethyl acetate (ratio by volume: 10:1) to obtain 18 g of the coupler having a melting point of 100° to 102° C.

Elemental Analysis for $C_{28}H_{34}Cl_5N_3O_2S$: Theoretical value (%): H: 5.24; C: 51.43; N: 6.43. Experimental value (%): H: 5.25; C: 51.72; N: 6.38.

SYNTHESIS EXAMPLE 3

Production of 1-(2,4,6-trichlorophenyl)-3-(2-chloro-5-tetradecanamidoanilino)-4-benzylthio-5-oxo-2-pyrazoline (Compound (1))

1-(2,4,6-trichlorophenyl)-3-(2-chloro-5-tetradecanamidoanilino)-5-oxo-2-pyrazoline (21.4 g) was dissolved in 80% ethanol (ratio by volume of water:20%), and 2.42 g of anhydrous potassium carbonate was added thereto. The solution was refluxed with heating. 8.2 g of S-benzylthioisothiourea hydrochloride was added to the solution and the solution was vigorously stirred for 3 hours. After confirming the conclusion of the reaction by thin film chromatography, the reaction container was cooled with water. The formed crystals were separated by filtration and dissolved in 100 ml of hot ethanol. Insoluble materials were separated by filtration, and the filtrate was cooled. The resulting colorless crystals were Compound (1). The melting point was 182° to 185° C. and the yield was 12 g.

Elemental Analysis for $C_{36}H_{40}N_4O_2SCl_4$: Theoretical value (%): H: 5.49; C: 58.56; N: 7.62. Experimental value (%): H: 5.40; C: 58.49; N: 7.64.

SYNTHESIS EXAMPLE 4

Production of 3-[3-(2,4-di-tert-amylphenoxy)acetamido]-benzamido-1-(2,4,6-trichlorophenyl)-4-ethylthio-2-pyrazoline-5-one (Compound (23))

Step (1):
Synthesis of S-{3-[3-(2,4-di-tert-amylphenoxy)acetamido]benzamido-1-(2,4,6-trichlorophenyl)-2-pyrazoline-5-one-4-yl}isothiuronium hydrobromide 50 g of 3-[3-(2,4-di-tert-amylphenoxy)acetamido]benzamido-4-bromo-1-(2,4,6-trichlorophenyl)-2-pyrazoline-5-one and 5.5 g of thiourea were dissolved in 250 ml of methanol. The resulting solution was stirred at room temperature (20° C.) for 1 hour. The reaction mixture was slowly added to 500 ml of water with stirring, and the separated solid was separated by filtration and dried. Thus, 55 g of the desired white solid was obtained.

Step (2):
Synthesis of 3-[3-(2,4-di-tert-amylphenoxy)acetamido]-benzamido-1-(2,4,6-trichlorophenyl)-4-mercapto-2-pyrazoline-5-one 16 g of potassium hydroxide was dissolved in 400 ml of methanol. After the atmosphere of this reaction container was replaced with nitrogen by introducing nitrogen gas thereto, 55 g of the isothiuronium salt obtained by the Step (1) was added in a powdery state thereto. The mixture was stirred at room temperature for 1 hour. The reaction mixture was added slowly to 800 ml of 1 N diluted hydrochloric acid with stirring, and the separated solid was filtered and dried. Thus, 48 g of the desired light yellow solid was obtained. This solid was used for the following step without purifying.

Step (3):
Synthesis of 3-[3-(2,4-di-tert-amylphenoxy)acetamido]-benzamido-1-(2,4,6-trichlorophenyl)-4-ethylthio-2-pyrazoline-5-one (Compound (23))

12 g of potassium hydroxide was dissolved in 400 ml of methanol. After the atmosphere of the reaction container was replaced with nitrogen by introducing a nitrogen gas thereto, 48 g of 3-[3-(2,4-di-tert-amylphenoxy)-acetamido]benzamido-1-(2,4,6-trichlorophenyl)-4-mercapto-2-pyrazoline-5-one obtained in the Step (2) was added as a powder and dissolved. 12.5 g of ethyl iodide was then added thereto. This solution was stirred at room temperature for 1 hour. After adding 1 l of ethyl acetate, the mixture was poured into a separating funnel and washed with 1 l of water. After the oil layer was separated and washed with 1 N diluted hydrochloric acid, it was washed twice further with 1 l of water. The oil layer was dried with anhydrous sodium sulfate. Ethyl acetate was then removed by distillation under a reduced pressure and the residue was recrystallized from acetonitrile to obtain 36 g of the desired product. The melting point was 138° to 140° C.

SYNTHESIS EXAMPLE 5

Synthesis of 3-[3-(2,4-di-tert-amylphenoxy)acetamido]-benzamido-4-carbamoylmethylthio-1-(2,4,6-trichlorophenyl)-2-pyrazoline-5-one (Compound (24))

The same procedure was carried out as in Synthesis Example 4, except that 11 g of chloroacetamide was used instead of ethyl iodide in the Step (3). Recrystallization was carried out using a mixture of acetonitrile and ethyl acetate to obtain 32 g of the desired coupler. The melting point was 157° to 159° C.

SYNTHESIS EXAMPLE 6

Synthesis of 3-[3-(2,4-di-tert-amylphenoxy)acetamido]-benzamido-1-(2,4,6-trichlorophenyl)-4-(2-methanesulfonamido)-ethylmercapto-2-pyrazoline-5-one (Compound (25))

22 g of S-{3-[3-(2,4-di-tert-amylphenoxy)acetamido]-benzamido-1-(2,4,6-trichlorophenyl)-2-pyrazoline-5-one-4yl}isothiuronium salt obtained in the Step (1) of Synthesis Example 4 was dissolved in 100 ml of methanol in the nitrogen substituted reaction container. To this solution, a solution prepared by dissolving 7.4 g of potassium hydroxide in 40 ml of methanol was added. After stirring at room temperature for 1 hour, 6.3 g of 2-methanesulfonamidoethyl chloride was added thereto. The mixture was stirred at room temperature for 2 hours. After adding 1 l of ethyl acetate, the mixture was poured into a separating funnel and washed with 1 l of water. The oil layer was separated and washed with 1 N diluted hydrochloric acid and then with water. It was then dried with anhydrous sodium sulfate. Ethyl acetate was removed by distillation under a reduced pressure and the residue was recrystallized with acetonitrile to obtain 15 g of the desired product. The melting point was 147° to 149° C.

A preferred amount of the coupler per mol of silver halide is about 0.005 to 0.5 mol, preferably about 0.01 to 0.1 mol in a color negative film or a color reversal photographic material and about 0.125 to 0.5 mol in a color paper or a color positive photographic material.

The couplers of the present invention are preferably located in a green sensitive silver halide emulsion layer. When the green sensitive layer consists of a plurality of layers, the coupler may be contained in each layer or in only one or more layers of the green sensitive unit.

The couplers of the present invention can be used by dissolving them in alkyl phosphate type solvents having a high boiling point such as dioctylbutyl phosphate as described in U.S. Pat. No. 3,676,137, solvents having a high boiling point such as tri-o-cresyl phosphate, dibutyl phthalate, diethyllaurylamide, 2,4-diethyldodecanamide, 2,4-diallyl phenol or materials described as "Improved photographic dye-image stabilizing solvents" in *Product Licensing Index*, Vol. 83 pp. 26-29 (March, 1971) and/or solvents having a low boiling point such as ethyl acetate or tetrahydrofuran as described in U.S. Pat. Nos. 2,801,170, 2,801,171, and 2,946,360.

The amount of high boiling point solvents is in a range of about 0 to 500% by weight and depends on the 5-pyrazolone coupler (the total amount when a plurality of couplers are used). Preferably, it is at most 300% by weight.

Preferably the coupler solution is once dispersed in an aqueous solution of gelatin and the resulted dispersion is added to silver halide emulsions.

Further, dispersion of the couplers may be carried out by processes described in Japanese Patent Application (OPI) Nos. 74538/74 (The term "OPI" as used herein refers to a "published unexamined Japanese patent application"), 19534/76 and 25133/76.

As binders or protective colloids for photographic emulsions, gelatin is advantageously used, but it is well known that other hydrophilic colloids may be used. For example, it is possible to use proteins such as gelatin derivatives, graft polymers of gelatin and other high molecular materials, albumin or casein, etc; sugar derivatives such as cellulose derivatives such as hydroxyethyl cellulose, carboxymethyl cellulose or cellulose sulfate, etc., sodium alginate or starch derivatives, etc.; and various synthetic hydrophilic high molecular substances such as homo- or copolymers, for example, polyvinyl alcohol, polyvinyl alcohol partial acetal, poly-N-vinylpyrrolidone, polyacrylic acid, polymethacrylic acid, polyacrylamide, polyvinyl imidazole or polyvinyl pyrazole, etc.

As the gelatin, not only lime-treated gelatin but also acid-treated gelatin or enzyme-treated gelatin as described in *Bull. Soc. Sci. Photo. Japan,* No. 16, page 30 (1966) may be used. Further, hydrolyzed products and enzymatic decomposition products of gelatin may be used. As the gelatin derivatives, there are those prepared by reacting gelatin with various compounds such as acid halides, acid anhydrides, isocyanates, bromoacetic acid, alkane sultones, vinyl sulfonamides, maleinimides, polyalkylene oxides or epoxy compounds, etc. Examples of this have been described in U.S. Pat. Nos. 2,614,928, 3,132,945, 3,186,846 and 3,312,553, British Pat. Nos. 861,414, 1,033,189 and 1,005,784 and Japanese Patent Publication No. 26845/67, etc.

Graft polymers of gelatin include those prepared by grafting homo- or copolymers of vinyl monomers such as acrylic acid, methacrylic acid, derivatives thereof such as esters or amides, acrylonitrile or styrene, etc., on gelatin. Particularly, graft polymers prepared using polymers compatible in some degree with gelatin, such as acrylic acid, methacrylic acid, acrylamide, methacrylamide or hydroxyalkyl methacrylate, etc., are preferred. Examples of these have been described in U.S. Pat. Nos. 2,763,625, 2,831,767 and 2,956,884.

Typical synthetic hydrophilic high molecular substances, for example, a polyvinyl alcohol, a polyvinylpyrrolidone, etc., are described in, for example, German Patent Application (OLS) No. 2,312,708, U.S. Pat. Nos. 3,620,751 and 3,879,205 and Japanese Patent Publication No. 7561/68.

Conventional silver halides can be used with the coupler of the present invention including a silver bromide, a silver chloride or a silver iodide or combinations thereof. In a negative type photographic material silver iodobromide is preferred wherein the composition of iodine is preferably 3 to 7 mol%. In a photographic paper silver iodochlorobromide or silver chloride is preferred, wherein the chlorine content is about 1 to 60 mol%, the bromine is about 40 to 99 mol% and the iodine is about 0 to 1 mol%.

In producing color photographic sensitive materials of the present invention, known ring opened ketomethylene type couplers can be used as yellow forming couplers. Among them, benzoylacetanilide type and pivaloylacetanilide type compounds are advantageously used. Examples of the yellow forming couplers are described in U.S. Pat. Nos. 2,875,057, 3,265,506, 3,408,194, 3,551,155, 3,582,322, 3,725,072 and 3,891,445, German Pat. No. 1,547,868, and German Patent Application (OLS) Nos. 2,213,461, 2,219,917, 2,261,361, 2,263,875 and 2,414,006.

The 5-pyrazolone type magenta couplers in the present invention may be used alone or in combinations of two or more. Further, the 5-pyrazolone type magenta couplers of the invention may be used together with other 5-pyrazolone type magenta couplers, imidazolone type couplers and cyanoacetyl compounds. Examples of these substances have been described in, for example, U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German Patent Application (OLS) Nos. 2,408,665, 2,417,945, 2,418,959 and 2,424,467 and Japanese Patent Publication No. 6031/65. The preferred amount of other coupler or couplers is 0.1 to 100 mols, preferably 1 to 10 mols per mol of the coupler of the present invention.

In producing color photographic sensitive materials of the present invention, phenol type compounds and naphthol type compounds can be used as cyan forming couplers. Examples of these are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383 and 3,767,411, German Patent Application (OLS) Nos. 2,414,830 and 2,454,329 and Japanese Patent Application (OPI) No. 59838/73.

As colored couplers, it is possible to use those described in, for example, U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77 and German Patent Application (OLS) No. 2,418,959.

The DIR couplers described in, for example, U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454 and Japanese Patent Application (OPI) No. 69624/77 can be used also.

The photosensitive materials may contain compounds which release a development restrainer upon development other than the DIR couplers. For example, compounds described in U.S. Pat. Nos. 3,297,445 and 3,379,529 and German Patent Application (OLS) No. 2,417,914 can be used.

Two or more of the above-described couplers can be contained in the same layer. Two or more layers may contain the same coupler.

The photosensitive materials of the present invention may be processed in a conventional manner after exposure. Further, they may be processed by a color intensification treatment using cobalt (III) complex salts described in Japanese Patent Application (OPI) Nos. 9278/73, 9729/73, 48130/73, 84229/74, 48239/74, 84240/74, 97614/74, 102340/74 and 102341/74, by a color intensification treatment with using peroxides described in German Patent Application (OLS) Nos. 1,813,920, 1,950,102, 1,955,901, 1,961,029, 2,044,833, 2,044,993, 2,056,360, 2,056,359 and 2,120,991, or by a color intensification treatment using perhalogenic acid salts described in Japanese Patent Application (OPI) Nos. 53826/76 and 99022/76. The above-described intensifiers may be added to the color development bath or to the intensification bath using after color development.

The conventional color processing comprises a color development step and a desilvering step (bleaching and fixation which may be carried out in separate baths or in one bath which is called "bleach-fix bath"). In order to stabilize the images, a stabilization bath having a low pH can be used before drying after fixation.

Preferred color developing agents used for these processings are p-phenylenediamine derivatives, examples of which include 2-methyl-4-(N,N-diethyl)aniline hydrochloride, 4-[N-ethyl-N(β-hydroxyethyl-)amino]aniline sulfate, 2-methyl-4-[N-ethyl-N-(β-hydroxyethyl)amino]aniline sulfate, N-ethyl-N-(β-methanesulfonamidoethyl)-3-methyl-4-amino-aniline sesquisulfate monohydrate described in U.S. Pat. No. 2,193,015, 2-(β-methanesulfonamidoethyl)-4-N,N-diethylaniline sulfate described in U.S. Pat. No. 2,592,364, N,N-dimethyl-p-phenylenediamine hydrochloride, and 4-amino-3-methyl-N-ethyl-N-methoxyethylaniline, 4-amino-3-methyl-N-β-ethoxyethylaniline and 4-amino-3-methyl-N-ethyl-N-β-butoxyethylaniline and salts of them (for example, sulfates, hydrochlorides, sulfites and p-toluenesulfonates, etc.) described in U.S. Pat. Nos. 3,656,950 and 3,698,525.

The developing solution may contain conventional additives such as sodium hydroxide, potassium hydroxide, sodium carbonate or potassium carbonate as alkali agents or buffer agents, sulfites, bromides or iodides of alkali metals, benzylalcohol or chelating agents, etc., for conventional purposes.

The bleaching bath may contain bleaching agents such as ferricyanides, bichromates, EDTA.Fe salt or cobalt hexamine chloride. Further, the fixing bath may contain fixers such as sodium thiosulfate, ammonium thiosulfate or potassium thiocyanate, etc. Further, as the bleach-fix bath, that described in U.S. Pat. No. 3,582,322 may be used.

The present invention will now be described in more detail by reference to the following examples.

EXAMPLE 1

11.9 g of Compound (1), 10.7 g of Compound (12) and 11.7 g of Compound (29) as the magenta coupler were dissolved respectively in a mixture of 10 ml of tricresyl phosphate and 20 ml of ethyl acetate. This solution was dispersed in 80 g of a 10% solution of gelatin containing sodium dodecylbenzenesulfonate. The resulting emulsified dispersion was mixed with 145 g of green-sensitive silver chlorobromide (Br: 70% by mol) (containing 7 g as Ag), and the mixture to which sodium dodecylbenzenesulfonate was added as a coating assistant was applied to paper base both surfaces of which were laminated with polyethylene, and dried.

To the resulting layer, a gelatin protective layer (gelatin: 1,000 mg/m²) was applied to produce Sample (A), Sample (B) and Sample (C).

The following three couplers were used as couplers for comparison.

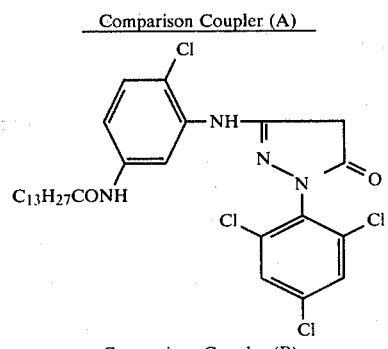

Comparison Coupler (A)

Comparison Coupler (B)

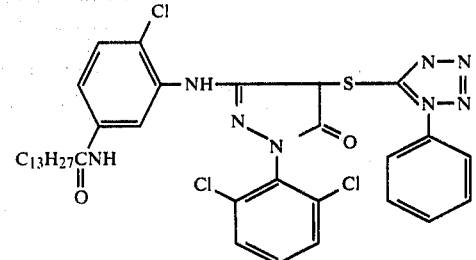

Comparison Coupler (C)

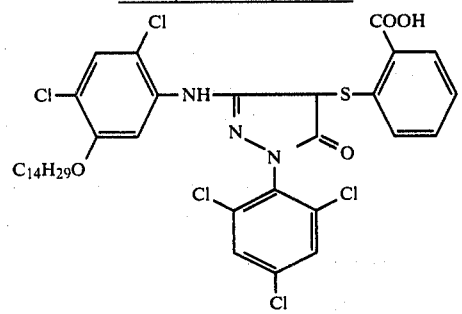

Using 10.0 g of the Comparison Coupler (A), 12.6 g of the Comparison Coupler (B) and 12.8 g of the Comparison Coupler (C), the same procedure as described above was carried out to produce Samples (D), (E) and (F), respectively.

The above described Samples (A) to (F) were exposed to light by a sensitometer for 1 second at 1,000 lux and processed as follows.

| Processing Step | Temperature (°C.) | Time |
|---|---|---|
| Color development | 33 | 3 min and 30 sec |
| Bleach-fixation | 33 | 1 min and 30 sec |
| Water wash | 30 | 3 min |
| Drying | | |

Above, the following liquid processing compositions were used.

| Color Development: | |
|---|---|
| Benzyl Alcohol | 15 ml |
| Sodium Sulfite | 5 g |
| KBr | 0.5 g |
| Hydroxylamine Sulfate | 3 g |
| N-Ethyl-N-[β-(methanesulfonamidoethyl)]-p-phenylenediamine | 6 g |
| Diethylene Glycol | 5 ml |
| NaOH | 4 g |
| Water to make 1 l (pH: 10.1) | |
| Bleach-Fix: | |
| (NH₄)₂S₂O₃ (70% by weight) | 160 ml |
| NH₄Fe(EDTA) | 50 g |
| EDTA . Na₂ | 3 g |
| Sodium Sulfite | 12 g |
| Water to make 1 l (pH: 6.8) | |

The results are shown in Table 1.

TABLE 1

| Optical Density | Sample | | | | | |
|---|---|---|---|---|---|---|
| | A (invention) | B (invention) | C (invention) | D (comparison) | E (comparison) | F (comparison) |
| $D_{max}$ | 1.80 | 1.95 | 1.90 | 1.50 | 0.40 | 0.10 |
| $D_{min}$ | 0.07 | 0.09 | 0.09 | 0.08 | 0.07 | 0.07 |

$D_{max}$ is the maximum optical density of the magenta image and $D_{min}$ is the minimum optical density thereof. Using these samples, the amounts of developed silver in case of $D_{max}$ were measured. The ratios of the amount of the dye actually formed to the theoretical amount of the dye in case of forming ¼ mol of dye per mol of the developed silver are shown in Table 2 as color formation efficiency.

TABLE 2

| | Sample | | | | | |
|---|---|---|---|---|---|---|
| | A | B | C | D | E | F |
| Color Formation Efficiency | 70% | 85% | 80% | 45% | 30% | 40% |

It is apparent from Tables 1 and 2 that dye densities increase in case of Samples (A), (B) and (C) by which the color formation efficiency increases. In the case of Samples (E) and (F) in which couplers having a heterocyclic thio group or an arylthio group are used, high $D_{max}$ cannot be obtained because the released heterocyclic thio group or arylthio group inhibits development.

Then, an ultraviolet ray absorbing filter (C-40) produced by Fuji Photo Film Co. which absorbs light of less than 400 nm was put on Samples (A) to (D), and a fading test was carried out for 2 weeks using a fluorescent light fading tester (20,000 lux). The results are shown in Table 3.

TABLE 3

| Sample | Variation of Yellow Density | Change in Magenta Density (initial density: 1.5) |
|---|---|---|
| A | +0.11 | −0.35 |
| B | +0.12 | −0.20 |
| C | +0.10 | −0.30 |
| D | +0.10 | −0.40 |

It is understood from these results that Samples (A) to (C) using the couplers of the present invention form images having excellent light fastness.

Further, after Samples (A) to (D) were exposed to light by a sensitometer, they were put in an airtight container containing 100 ml of a glycerine solution conditioned at 40° C. and 70% relative humidity (R.H.) to which 1 ml of 37% formalin was added. After 3 days, they were subjected to color development. In order to compare, a formaldehyde nonprocessing sample which was merely exposed to light was subjected to color development.

$$\text{Density Reduction Ratio} = \frac{\text{Color density of formaldehyde processing sample}}{\text{Color density of formaldehyde nonprocessing sample}}$$

Results are shown in Table 4.

TABLE 4

| Sample | Aldehyde Durability |
|---|---|
| A | 0.90 |
| B | 0.85 |
| C | 0.85 |
| D | 0.60 |

As is apparent from Table 4, improvement of the formaldehyde durability was observed in Samples (A) to (C) as compared with Sample (D).

It is understood from these results that Samples (A) to (C) using the couplers of the present invention form images having excellent fastness to light.

EXAMPLE 2

Using Compounds (1), (12) and (29), compositions for the third layer shown in the following table were produced according to Example 1, the multilayer Samples (G), (H) and (I) were produced as shown in the following table. Further, similar multilayer Sample (J) was produced using Comparison Coupler (A) from Example 1.

| | |
|---|---|
| 6th layer | Gelatin (application amount: 1,000 mg/m²) |
| 5th layer | Red-sensitive layer: Silver chlorobromide emulsion (Br: 50% by mol, application amount: silver 300 mg/m²), Cyan coupler*¹ (application amount: 400 mg/m²), Gelatin (application amount: 1,000 mg/m²) and Coupler solvent*² (application amount: 200 mg/m²). |
| 4th Layer | Intermediate layer: Gelatin (application amount: 1,200 mg/m²) and Ultraviolet ray absorbing agent (application amount: 1,000 mg/m²). |
| 3rd Layer | Green-sensitive layer: Silver chlorobromide emulsion (Br: 50% by mol, application amount: silver 285 mg/m²), Magenta coupler (application amount: below), Gelatin (application amount: 1,000 mg/m²) and Coupler solvent*³ (application amount: 200 mg/m²). |
| 2nd Layer | Intermediate layer: Gelatin (application amount: 1,000 mg/m²). |
| 1st Layer | Blue-sensitive layer: Silver chlorobromide emulsion (Br: 80% by mol, application amount: 400 mg/m²), Yellow coupler*⁴ (application amount: 300 mg/m²), Gelatin (application amount: 1,200 mg/m²) and Coupler solvent*² (application amount: 150 mg/m²). |
| Base*⁵ | |
| *1 Coupler: | 2-[α-(2,4-di-t-amylphenoxy)butanamido]-4,6-dichloro-5-methylphenol. |
| *2 Solvent: | Dibutyl phthalate |
| *3 Coupler solvent: | Tricresyl phosphate |
| *4 Coupler: | α-Pivaloyl-α-(2,4-dioxo-5,5'-dimethyl-oxazolidine-3-yl)-2-chloro-5-[α-(2,4-di-t-amylphenoxy)butanamido]acetanilide. |
| *5 Base: | Paper base both surfaces of which were laminated with polyethylene containing dispersed titanium dioxide. |

The magenta couplers in Samples (G) to (J) are used each in the same molar amount. Accordingly, the amount of magenta coupler is 240 mg/m² in Sample (G), 215 mg/m² in Sample (H), 235 mg/m² in Sample (I) and 200 mg/m² in Sample (J).

A green filter (SP-2) produced by Fuji Photo Film Co., Ltd. was placed on these samples, and they were exposed to light for 1 second at 1,000 lux through an optical wedge.

These samples were processed as in Example 1. The results measured are shown in the following table.

TABLE 5

| Optical Density | Sample | | | |
|---|---|---|---|---|
| | (G) | (H) | (I) | (J) |
| $D_{max}$ | 1.90 | 2.05 | 2.00 | 1.60 |
| $D_{min}$ | 0.08 | 0.09 | 0.08 | 0.08 |

It is understood from these results that Samples (G) to (I) according to the present invention have a high color density (color formation efficiency).

EXAMPLE 3

Multilayer samples (G) to (J) of Example 2 were processed as follows. Namely, the amount of sodium hydroxide in the color developing solution in Example 1 was adjusted to prepare three color developing solutions having pH 9.8, 10.1 and 10.40, and color development was carried out. Then, the same procedure as in Example 1 was carried out. The results obtained are shown in Table 6. In the table, the change in the sensitivity of these samples caused by variation of the pH of the color developing solution are shown as the difference based on the sensitivity in case of carrying out color development at pH 10.1.

Further, the sensitivity was measured as log E on the point of a characteristic curve of optical sensitivity which was 0.50 higher than $D_{min}$.

TABLE 6

| pH of Color Developing Solution | Shift of Sensitivity (Δ log E) | | | |
|---|---|---|---|---|
| | Sample (G) | Sample (H) | Sample (I) | Sample (J) |
| 9.8 | −0.03 | −0.02 | −0.03 | −0.07 |
| 10.1 | 0 | 0 | 0 | 0 |
| 10.4 | +0.02 | +0.02 | +0.02 | +0.05 |

It is understood that the Samples (G), (H) and (I) containing 2-equivalent magenta couplers of the present invention are very stable to variations in pH of the color developing solution, because the change in sensitivity caused by changes in the pH value of the color developing solution is only about ½ of that in Comparison Sample (J).

EXAMPLE 4

Sample K: The following 1st layer to 4th layer were applied in turn to a transparent cellulose triacetate film base and dried to obtain a sample. The coating solutions used for each layer had the following compositions and were produced as follows.

1st Layer:
Red-sensitive emulsion layer: 1 kg of a high speed silver iodobromide emulsion prepared by a conventional process (silver content: 0.6 mol, iodine content: 6% by mol) was spectrally sensitized using Sensitizing Dye I in the amount of $4 \times 10^{-5}$ mols/mol of silver and Sensitizing Dye II in the amount of $1 \times 10^{-5}$ mols/mol of silver. 100 g of Coupler (D) was dissolved in a mixture of 100 ml of tricresyl phosphate and 200 ml of ethyl acetate. This solution was dispersed in 1 kg of a 10% aqueous solution of gelatin using 4 g of sodium nonylbenzenesulfonate (surface active agent). 550 g of the resulting cyan coupler emulsion was added to the above-described spectrally sensitized silver iodobromide emulsion with stirring. To the resulting mixture, 2 g of sodium 2,4-dichloro-6-hydroxytriazine was added as a hardening agent as an aqueous solution. The prepared coating solution was applied to a transparent cellulose triacetate film so as to be 1.5 g/m² of the silver content.

2nd Layer:
Intermediate layer: 50 g of 2,5-di-t-octylhydroquinone was dissolved in 100 ml of tricresyl phosphate, and the solution was dispersed in 1 kg of a 10% aqueous solution of gelatin by the same manner as in Emulsion I. 250 g of the resulting emulsion and 2 g of sodium 2,4-dichloro-6-hydroxytriazine (as an aqueous solution) were added to 1 kg of a 10% aqueous solution of gelatin. The mixture was applied to form a layer a 1.5 microns dry thickness.

3rd Layer:
Green-sensitive emulsion layer: 1 kg of a high speed silver iodobromide emulsion (similar to that of the 1st layer) was spectrally sensitized using Sensitizing Dye III in the amount of $3 \times 10^{-5}$ mols/mol of silver and Sensitizing Dye IV in the amount of $1 \times 10^{-5}$ mols/mol of silver. Using 100 g of Coupler (1), Magenta Coupler Emulsion (I) was prepared in the same manner as the above-described cyan coupler emulsion. To the above-described spectrally sensitized silver iodobromide emulsion, 700 g of the Magenta Coupler Emulsion (I) was added and 2 g of sodium 2,4-dichloro-6-hydroxytriazine was then added as an aqueous solution with stirring.

4th Layer:
Protective layer: 2 g of sodium 2,4-dichloro-6-hydroxytriazine was added to 1 kg of a 10% aqueous solution of gelatin. The solution was applied so as to form a layer 1.5 microns in dried thickness.

Sample L:
Preparaton was carried out in the same manner as in Sample K except that Magenta Coupler Emulsion (II) containing Comparison Coupler (A) described in Example 1 was used instead of Magenta Coupler Emulsion (I) in Sample K.

The compounds used above are:

| | |
|---|---|
| Sensitizing Dye I: | Anhydro-5,5'-dichloro-3,3'-di-sulfopropyl-9-ethyl-thiacarbocyanine hydroxide pyridinium salt. |
| Sensitizing Dye II: | Anhydro-9-ethyl-3,3'-di-(3-sulfopropyl)-4,5,4',5'-dibenzothiacarbocyanine hydroxide triethylamine salt. |
| Sensitizing Dye III: | Anhydro-9-ethyl-5,5'-dichloro-3,3'-sulfopropyloxacarbocyanine sodium salt. |
| Sensitizing Dye IV: | Anhydro-5,6,5,6-tetrachloro-1,1-diethyl-3,3-sulfopropoxyethoxyethyl-imidazolocarbocyanine hydroxide sodium salt. |
| Coupler D: | 1-Hydroxy-N-[γ-(2,4-di-tert-amyl-phenoxy)propyl]-2-naphthamide. |

The image sharpness of the resulting multilayer samples was evaluated. Namely, it was carried out by measuring the response function (Modulation Transfer Function: referred to as MTF hereinafter) and comparing values of MTF at a certain frequency. Measurement of MTF was carried out according to the description of "Hihakaidokensa" (Nondestructive Test), Vol. 16, pp. 472–482 (1967) written by Masao Takano and Kunio Fujimura. The exposure was carried out using white light and the measurement was carried out through a red or green filter. The development was carried out at 38° C. as follows.

| | |
|---|---|
| 1. Color development | 3 minutes and 15 seconds |
| 2. Bleaching | 6 minutes and 30 seconds |
| 3. Water wash | 3 minutes and 15 seconds |

| -continued | |
|---|---|
| 4. Fixation | 6 minutes and 30 seconds |
| 5. Water wash | 3 minutes and 15 seconds |
| 6. Stabilizing | 3 minutes and 15 seconds |

The compositions of the processing solutions used in each step were as follows.

| Color Developing Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-$\beta$-hydroxyethylamino)-2-methylaniline Sulfate | 4.5 g |
| Water to make | 1 l |
| Bleaching Solution | |
| Ammonium Bromide | 160.0 g |
| Aqueous Ammonia Solution (28%) | 25.0 ml |
| Sodium Iron Ethylenediaminetetraacetate | 130.0 g |
| Glacial Acetic Acid | 14.0 ml |
| Water to make | 1 l |
| Fixing Solution | |
| Sodium Tetrapolyphosphate | 2.0 g |
| Sodium Sulfite | 4.0 g |
| Ammonium Thiosulfate (70%) | 175.0 ml |
| Sodium Bisulfite | 4.6 g |
| Water to make | 1 l |
| Stabilizing Solution | |
| Formalin | 8.0 ml |
| Water to make | 1 l |

The resulting MTF values are shown in Table 7. In Table 7, MTF values at the frequency of 20/1 nm are shown. These values indicate that delineation of fine drawings. The higher the MTF value, the higher the image sharpness.

TABLE 7

| | MTF Values | |
|---|---|---|
| Sample | Measurement through Red Filter | Measurement through Green Filter |
| K | 82 | 88 |
| L | 75 | 85 |

As shown in Table 7, the sharpness of the green-sensitive layer and that of the red-sensitive layer in Sample K are remarkably improved as compared with Sample L and, particularly, it is understood that sharpness of the red-sensitive layer as the lowest layer is highly improved.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material which comprises a photographic layer containing at least one coupler represented by the following general formula (I):

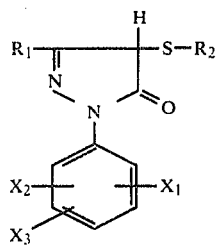

where $R_1$ represents an anilino group, an acylamino group or a ureido group, $R_2$ represents an alkyl group which is substituted by at least one member selected from the group consisting of a halogen atom, a nitro group, a cyano group, an aryl group, an alkoxy group, an aryloxy group, a carboxyl group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group and a hydroxy group, an aralkyl group or an alkenyl group, $X_1$, $X_2$ and $X_3$ each represents a hydrogen atom, an alkyl group, a halogen atom, an alkoxy group, an aryloxy group, an acylamino group, a carbamoyl group, a sulfamoyl group, a sulfonyl group, a cyano group or an alkoxycarbonyl group, and $X_1$, $X_2$ and $X_3$ may be the same or different.

2. The silver halide color photographic material of claim 1 wherein $R_1$ represents an anilino group which may be unsubstituted or substituted by at least one substituent selected from the group consisting of a halogen atom, an alkyl group, an aralkyl group, an alkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an alkylcarbonyloxy group, an arylcarbonyloxy group, a sulfamoyl group, a carbamoyl group, an alkylcarbonylamino group, an arylcarbonylamino group, a dialkylcarbonylamino group, a diarylcarbonylamino group, a ureido group, a thioureido group, a sulfonamino group, an alkoxycarbonylamino group, an aryloxycarbonylamino group, a heterocyclic ring group, an alkylsulfonyloxy group, an arylsulfonyloxy group, an alkylsulfonyl group, an arylsulfonyl group, an alkylthio group, an arylthio group, an alkylsulfinyl group, an arylsulfinyl group, an alkylamino group, a dialkylamino group, an anilino group, an N-arylamino group, an N-alkylanilino group, an N-alkylcarbonylanilino group, an N-arylcarbonylanilino group, an imido group, a 1-hydantoinyl group, a 2,4-dioxo-3-oxazolidinyl group and a hydroxy group.

3. The silver halide color photographic material of claim 1 wherein $R_1$ represents an acylamino group wherein said acylamino group represents an alkaneamido group or a benzamido group.

4. The silver halide color photographic material of claim 1 wherein $R_1$ represents a ureido group wherein said ureido group represents an alkylureido group, or a phenylureido group.

5. The silver halide color photographic material of claim 1, wherein when $R_2$ is said alkyl group the alkyl chain thereof has 1 to 22 carbon atoms.

6. The silver halide color photographic material of claims 1 or 5, wherein when $R_2$ is said alkyl group the alkyl chain thereof has 1 to 15 carbon atoms.

7. The silver halide color photographic material of claims 1 or 5, wherein when $R_2$ is said alkyl group the alkyl chain thereof has 1 to 5 carbon atoms.

8. The silver halide color photographic material of claim 1, wherein said photographic layer is a green-sensitive silver halide emulsion layer.

9. The silver halide color photographic material of claim 1, wherein said photographic layer is a hydrophilic colloid layer associated with a green-sensitive silver halide emulsion layer.

10. The silver halide color photographic material of claim 1, wherein $X_1$, $X_2$ and $X_3$ each represents a halogen atom, an alkyl group, an alkoxy group, an acylamino group, a cyano group or an alkoxycarbonyl group.

11. The silver halide color photographic material of claim 1, wherein said coupler is present in an amount of 0.005 to 0.5 mol per mol of silver halide.

12. The silver halide color photographic material of claim 1, wherein $R_1$ represents a phenylamino group, an o-chlorophenylamino group, a 2,4-dichlorophenylamino group, a 2,4-dichloro-5-methoxyphenylamino group, a 2-chloro-5-tetradecanamidophenylamino group, a 2-chloro-5-[α-(2,4-di-t-aminophenoxy)butyramido]phenylamino group, a 2-chloro-5-[(3-octadecenyl)succinimido]phenylamino group or a 2-chloro-5-{α-[(3-5-butyl-4-hydroxy)phenoxy]tetradecanamido}phenylamino group.

13. The silver halide color photographic material of claim 1, wherein $R_1$ represents an acetylamino group, a butyramido group, an α-(3-pentadecylphenoxy)-butyramido group, an n-tetradecanamido group, an α-(2,4-di-t-amylphenoxy)butyramido group, a 3-[α-(2,4-di-t-amylphenoxy)-butyramido]benzamido group, a benzamido group or a 3-acetylamidobenzamido group.

14. The silver halide color photographic material of claim 1, wherein $R_1$ represents a phenylureido group, a methylureido group or a 3-[α-(2,4-di-t-amylphenoxy)-butyramido]phenylureido group.

* * * * *